United States Patent
Hosoda et al.

(10) Patent No.: US 12,104,236 B2
(45) Date of Patent: Oct. 1, 2024

(54) SHAPE-MEMORY ALLOY AND SHAPE-MEMORY ALLOY WIRE

(71) Applicants: TOKYO INSTITUTE OF TECHNOLOGY, Tokyo (JP); TANAKA KIKINZOKU KOGYO K.K., Tokyo (JP)

(72) Inventors: Hideki Hosoda, Tokyo (JP); Akira Umise, Tokyo (JP); Kenji Goto, Kanagawa (JP)

(73) Assignees: TOKYO INSTITUTE OF TECHNOLOGY and, Tokyo (JP); TANAKA KIKINZOKU KOGYO K.K., Tokyo (JP)

( * ) Notice: Subject to any disclaimer, the term of this patent is extended or adjusted under 35 U.S.C. 154(b) by 1045 days.

(21) Appl. No.: 16/968,764

(22) PCT Filed: Feb. 28, 2019

(86) PCT No.: PCT/JP2019/007752
§ 371 (c)(1),
(2) Date: Aug. 10, 2020

(87) PCT Pub. No.: WO2019/168081
PCT Pub. Date: Sep. 6, 2019

(65) Prior Publication Data
US 2021/0010120 A1    Jan. 14, 2021

(30) Foreign Application Priority Data

Mar. 2, 2018  (JP) ................................. 2018-037895

(51) Int. Cl.
*C22F 1/00*   (2006.01)
*A61L 27/04*  (2006.01)
(Continued)

(52) U.S. Cl.
CPC ............ *C22F 1/006* (2013.01); *A61L 27/047* (2013.01); *A61L 27/50* (2013.01); *A61L 29/02* (2013.01);
(Continued)

(58) Field of Classification Search
CPC .... C22F 1/006; C22F 1/14; C22F 1/00; A61L 27/047; A61L 27/50; A61L 29/02;
(Continued)

(56) References Cited

U.S. PATENT DOCUMENTS

2012/0035632 A1   2/2012  Hamada et al.
2016/0362772 A1*  12/2016 Hosada ..................... C22C 1/02
2019/0030215 A1   1/2019  Okubo et al.

FOREIGN PATENT DOCUMENTS

CN    101565783 A    10/2009
JP    H03-13535 A    1/1991
(Continued)

OTHER PUBLICATIONS

Hosoda, Hideki et al. Effect of Al and Cu contents on Mechanical Properties of Au—Cu—Al Shape Memory Alloys, J. Japan Inst. Met. Mater. vol. 80, No. 1, Nov. 27, 2015 (Year: 2015).*

(Continued)

*Primary Examiner* — Brian D Walck
*Assistant Examiner* — Danielle Carda
(74) *Attorney, Agent, or Firm* — Foley & Lardner LLP (57) ABSTRACT

The present invention provides a shape-memory alloy including a Au—Cu—Al alloy having 20 at % or more and 40 at % or less Cu and 15 at % or more and 30 at % or less Al, with the balance being Au and inevitable impurities. The shape-memory alloy has a Vickers hardness of 360 Hv or less. The Au—Cu—Al alloy of the present invention is an alloy capable of developing both biocompatibility and a shape-memory effect, and further capable of achieving arti- (Continued)

factlessness in a magnetic environment. The Au—Cu—Al alloy can be produced by heat-treating a clad material formed of a combination of a hollow material made of a Au—Cu alloy and a core material made of metallic Al at 500° C. or more and 700° C. or less.

8 Claims, 3 Drawing Sheets

(51) Int. Cl.
| | |
|---|---|
| *A61L 27/50* | (2006.01) |
| *A61L 29/02* | (2006.01) |
| *A61L 29/14* | (2006.01) |
| *A61L 31/02* | (2006.01) |
| *A61L 31/14* | (2006.01) |
| *C22C 5/02* | (2006.01) |
| *C22F 1/14* | (2006.01) |

(52) U.S. Cl.
CPC ............ *A61L 29/14* (2013.01); *A61L 31/022* (2013.01); *A61L 31/14* (2013.01); *C22C 5/02* (2013.01); *C22F 1/14* (2013.01); *A61L 2400/16* (2013.01); *A61L 2430/12* (2013.01)

(58) Field of Classification Search
CPC ........ A61L 29/14; A61L 31/022; A61L 31/14; A61L 2400/16; A61L 2430/12; C22C 5/02; A61C 7/00; A61C 8/00; A61C 13/267; A61F 2/86; A61M 25/00; A61M 25/09
USPC ........................................................ 148/535
See application file for complete search history.

(56) References Cited

FOREIGN PATENT DOCUMENTS

| JP | 2014-084485 A | 5/2014 | | |
|---|---|---|---|---|
| JP | 2015-048485 A | 3/2015 | | |
| JP | 2018048485 A | * 3/2015 | ............... | C22C 1/02 |
| JP | 2017-158608 A | 9/2017 | | |
| WO | WO-2010/084948 A1 | 7/2010 | | |
| WO | WO-2019/039298 A1 | 2/2019 | | |

OTHER PUBLICATIONS

Pandhi, Mithil et al. Understanding the Basics of Commonly Used Wires in Interventional Radiology, Semin Intervent Radiol 2021; 38: 504-508 (Year: 2021).*

International Preliminary Report on Patentability dated Jun. 30, 2020 for corresponding International Patent Application No. PCT/JP2018/007752.

Written Reply to Written Opinion submitted on Mar. 24, 2020 for corresponding International Patent Application No. PCT/JP2019/007752.

Hosoda et al., "Effect of Al and Cu Contents on Mechanical Properties of Au—Cu—Al Shape Memory Alloys," J. Japan Inst. Met. Mater., vol. 80, No. 1, 2016, pp. 27-36.

International Searching Authority, "International Search Report," issued in connection with International Patent Application No. PCT/JP2019/007752, dated May 28, 2019.

International Searching Authority, "Written Opinion," issued in connection with International Patent Application No. PCT/JP2019/007752, dated May 28, 2019.

* cited by examiner

SHAPE-MEMORY ALLOY AND SHAPE-MEMORY ALLOY WIRE

RELATED APPLICATIONS

The present application claims priority under 37 U.S.C. § 371 to International Patent Application No. PCT/JP2019/007752, filed Feb. 28, 2019, which claims priority to and the benefit of Japanese Patent Application No. 2018-037895, filed on Mar. 2, 2018. The contents of these applications are hereby incorporated by reference in their entireties.

TECHNICAL FIELD

The present invention relates to a shape-memory alloy and a shape-memory alloy wire, which are suitable as materials for medical use. It specifically relates to a shape-memory alloy that is Ni-free and further is artifactless in a magnetic environment, and also to a shape-memory alloy wire. It further relates to a shape-memory alloy, whose transformation point can be reduced and which can be a superelastic alloy.

BACKGROUND ART

Conventionally, in the medical field, shape-memory alloys have been utilized. A shape-memory alloy is a metal alloy having such characteristics that at a temperature not lower than the transformation point, even when significantly deformed, the alloy can return to its the original shape. Then, among shape-memory alloys, an alloy having a transformation point near the ambient temperature range is called a superelastic alloy. Such shape-memory alloys and superelastic alloys are expected to be applied to constituent materials of instruments for medical use, such as catheters, stents, embolization coils, and guidewires.

Of alloys belonging to shape-memory alloys, Ni—Ti-based shape-memory alloys are particularly known in terms of practicality and the like. However, a Ni—Ti-based alloy contains Ni, which can cause a metal allergy, and thus is a material that lacks biocompatibility, that is, a characteristic that should be regarded as most important in the medical field. Therefore, an alloy material that is Ni-free and is also capable of developing shape-memory characteristics even at a temperature not higher than a biological body temperature has been developed.

As examples of studies about Ni-free shape-memory alloys or superelastic alloys in consideration of biocompatibility, the present applicant has disclosed a superelastic alloy obtained by adding Co and Mo or Nb to a Au-Ti-based shape-memory alloy (Patent Document 1), a superelastic alloy obtained by adding Fe or Co to a Au—Cu—Al-based shape-memory alloy (Patent Document 2), and the like. These alloys exclude Ni and yet have shape-memory characteristics, and further are also capable of developing superelasticity. The above alloys are also advantageous in that Au, which is a metal with excellent biocompatibility, is used as a constituent element.

RELATED ART DOCUMENT

Patent Documents

Patent Document 1: JP 2014-84485 A
Patent Document 2: JP 2015-48485 A

SUMMARY OF THE INVENTION

Problems to be Solved by the Invention

Incidentally, recently in the medical fronts, diagnosis/treatment using a magnetic resonance image processor (MRI) has been widely performed. In such diagnosis as using a magnetic apparatus, there has been a growing concern about effects due to a magnetic environment. As a problem caused by such effects, artifacts in MRI (false images) can be mentioned. An artifact is a phenomenon in which the metal materials constituting a medical instrument are magnetized by a magnetic environment, resulting in distortion in an MRI image of the peripheral region of the instrument. The occurrence of artifacts obstructs accurate diagnosis, treatment, or surgery.

In light of the latest progress of treatment/diagnosing methods in the medical fronts described above, as requirements for materials for medical use, in addition to biocompatibility (to make Ni-free) and appropriate shape-memory characteristics (decrease in the transformation temperature), artifactlessness in a magnetic environment has been newly demanded.

Here, the technical significance of the development of a shape-memory effect and that of artifactlessness will be examined. Because these phenomena are theoretically different from each other, their simultaneous realization is not necessarily easy. That is, the principle of a shape-memory effect is based on the phase transition phenomenon caused by martensite transformation and relates to the crystal structure of an alloy. Therefore, in consideration of the crystal structure of the alloy, constituent elements capable of decreasing the transformation temperature are employed for achievement. Then, if possible, the alloy is designed such that the transformation temperature is made within an ambient temperature range, whereby superelasticity can be developed.

Meanwhile, an artifact is a phenomenon attributable to the magnetization of a metal/alloy in a magnetic environment. That is, artifacts are related to the magnetizing characteristics (bulk susceptibility) of the metal or metal species constituting the alloy. This is a factor completely different from the principle of the shape-memory effect phenomenon (crystal structure).

Then, with respect to the problem with artifacts, the susceptibility does not only have to be reduced but also needs to be controlled depending on the intended use. In an apparatus for medical use, the susceptibility of its constituent materials needs to approximate the susceptibility of biological tissues. Specifically, the main constituent component of a biological tissue is water, and its susceptibility is required to approximate −9 ppm ($-9 \times 10^{-6}$).

In this respect, it can be said that conventional shape-memory alloys and superelastic alloys have achieved the simultaneous realization of biocompatibility and the development of a shape-memory effect or superelasticity. However, under the present conditions, the object including artifactlessness in addition to these characteristics has not yet been achieved.

The present invention has been accomplished against the above background, and discloses an alloy that has biocompatibility, is capable of developing a shape-memory effect, and is further capable of achieving artifactlessness in a magnetic environment. With respect to a shape-memory effect, an alloy whose transformation temperature can be reduced to an appropriate temperature, such as to a human body temperature or an ambient temperature range, for example, is disclosed. Further, the present invention also discloses characteristics necessary for processing such a shape-memory alloy into various instruments for medical use.

Means for Solving the Problems

As an alloy system capable of solving the above problems, the present inventors have focused on Au—Cu—Al alloys. As mentioned in the above Patent Document 2, a Au—Cu—Al alloy is an alloy capable of developing a shape-memory effect, and the alloy also has the possibility of developing superelasticity at ambient temperature. Further, because Ni is not a constituent element, the biocompatibility requirements are also met.

Then, Au that constitutes a Au—Cu—Al alloy has an important advantage for artifactlessness, which is an object of the present invention. That is, Au is a diamagnetic metal having a susceptibility of −34 ppm. As described above, as an artifactless material, it is suitable to have a susceptibility within a range close to the susceptibility of water (−9 ppm). Au is a metal whose susceptibility is close to this standard, and thus is a metal that can be regarded as a starting point for achieving the object of the present invention.

According to the study by the present inventors, the susceptibility of an alloy can be controlled according to the magnetic properties of constituent metals and their amounts (composition). As described above, the susceptibility of Au is −34 ppm. Therefore, by making a slight shift to the plus side, the susceptibility can be approximated to that of water (−9 ppm). Meanwhile, with respect to the constituent metals of a Au—Cu—Al alloy other than Au, the susceptibility of Al, which is a paramagnetic metal, is 16 ppm. Accordingly, as a result of alloying with Au, the susceptibility of the alloy can be adjusted to the plus side. In addition, the susceptibility of Cu, which is a diamagnetic metal, is −9 ppm, that is, near the desired value. Thus, as compared with Al, its effects on the susceptibility of the alloy are mild.

Against a background of such considerations, the present inventors have conducted extensive researches and found, with respect to a Au—Cu—Al alloy, an alloy in an appropriate composition range, which develops a useful shape-memory effect and also exhibits susceptibility that can be regarded as artifactless. Then, they have arrived at the present invention having a suitable Au—Cu—Al alloy configuration in terms of its production and processing into an instrument for medical use.

That is, the present invention is drawn to a shape-memory alloy including a Au—Cu—Al alloy having 20 at % or more and 40 at % or less Cu and 15 at % or more and 30 at % or less Al, with the balance being Au and inevitable impurities. The shape-memory alloy has a Vickers hardness of 360 Hv or less.

Hereinafter, the present invention will be described in further detail. The shape-memory alloy according to the present invention, which is composed of a Au—Cu—Al alloy and has been made artifactlessness, is an alloy containing Au as a main constituent element and also having Cu and Al added within suitable ranges. Then, with respect to the Au—Cu—Al alloy in a predetermined composition range, the hardness thereof is specified. Hereinafter, the constituent metals of the alloy will be described. Incidentally, hereinafter, unless otherwise clearly noted, "%" showing an alloy composition means "at %". In addition, the "susceptibility" of an alloy means bulk susceptibility.

In the Au—Cu—Al alloy according to the present invention, the added amount of Cu is specified to be 20 at % or more and 40 at % or less. Cu is a metal element that is mainly involved in the shape-memory effect or superelasticity of an alloy. When Cu is less than 20 at %, the development of a shape-memory effect becomes difficult. Then, when 40 at % is exceeded, the transformation temperature becomes too high, making it difficult to develop a shape-memory effect below a human body temperature. Cu is more preferably 25 at % or more and 35 at % or less.

In addition, the added amount of Al is specified to be 15 at % or more and 30 at % or less. In the present invention, Al is also an important constituent metal. Al is a metal element that is involved in a shape-memory effect and also has a relatively strong susceptibility adjustment action. Further, Al also affects the workability of an alloy. When Al is less than 15 at %, it becomes difficult to develop a shape-memory effect at an appropriate temperature, and the resulting susceptibility adjustment action is also poor. Then, when Al is more than 30 at %, the transformation temperature becomes excessively low, and also the hardness becomes too high, resulting in extreme deterioration of workability. Al is more preferably 18 at % or more and 30 at % or less.

Based on the added amounts Cu and Al described above, the balances are specified to be Au and inevitable impurities. The Au concentration is more preferably 40 at % or more and 57 at % or less.

In addition, as inevitable impurities in the alloy according to the present invention, Cr, Mg, W, Si, and the like may be contained. These inevitable impurity elements are each preferably 0 ppm or more and 50 ppm or less, and more preferably 0 ppm or more and 30 ppm or less.

Then, the shape-memory alloy composed of a Au—Cu—Al of the present invention has a Vickers hardness of 360 Hv or less. According to the study by the present inventors, the toughness of the present inventive Au—Cu—Al alloy is relatively poor, and its workability may be poor depending, for example, on the processing history and thermal history. Meanwhile, the present invention is expected as a constituent material of an instrument for medical use, and is often processed into the shape of a wire, for example. Thus, in the present invention, the hardness is specified for covering workability. An alloy having a Vickers hardness of more than 360 Hv has deteriorated workability and is difficult to process into an instrument for medical use. Incidentally, the Vickers hardness of the shape-memory alloy composed of a Au—Cu—Al alloy of the present invention is preferably 130 Hv or more.

In consideration of the ease of measurement, in the present invention, the Vickers hardness is specified as a hardness value. The measuring apparatus for Vickers hardness can be selected depending on the dimension/form of the material, and may be a Vickers hardness meter, a micro Vickers hardness meter, or the like. The load at the time of hardness measurement also depends thereon, but the measurement is performed generally under a load of 10 gf or more and 300 gf or less.

The shape-memory alloy according to the present invention described above is an alloy that can achieve the development of a shape-memory effect or superelasticity at a human body temperature or in an ambient temperature range and also artifactlessness in a magnetic environment. Here, for the development of a shape-memory effect in the human body's internal environment, the alloy of the present invention preferably has a transformation temperature (Ms point) of 313 K or less.

Meanwhile, with respect to artifactlessness, the present inventive shape-memory alloy preferably has a bulk susceptibility of −24 ppm or more and 6 ppm or less. Relative to the biological bulk susceptibility −9 ppm, ±15 ppm is a suitable range. Within this range, in a magnetic environment such as MRI, the effect due to artifacts can be sufficiently reduced.

Incidentally, as described above, the shape-memory alloy according to the present invention needs to achieve the requirements of both the shape-memory effect development and magnetizing characteristics described above. In order to make these characteristics suitable at the same time, it is preferable that the alloy materials have excellent homogeneity. As the homogeneity, for example, the homogeneity of the alloy composition can be mentioned. As a specific example, reduced variation in the concentrations of constituent metals in the alloy can be mentioned. The variation can be evaluated, for example, as follows. In an arbitrary part of an alloy material to be evaluated, its longitudinal cross-section (i.e. cross-section parallel to the wire length direction) and transverse cross-section (i.e. cross-section perpendicular to the wire length direction) are subjected to composition analysis. In this composition analysis, in the longitudinal cross-section and the transverse cross-section, at least five points including a central part and a part near the edge are analyzed for the concentration (at %) of at least one of Au, Cu, and Al, and the standard deviation thereof is determined. Then, it is preferable that in at least one of the longitudinal cross-section and the transverse cross-section, the standard deviation of the concentration of at least one element is 1.0 at % or less. The standard deviation of the composition is more preferably 0.8 at % or less, and still more preferably 0.6 at % or less. Incidentally, as the object to be analyzed, the Au concentration is preferably selected.

The shape-memory alloy material made of a Au—Cu—Al alloy according to the present invention described above is suitable as a constituent material of an instrument for medical use, such as a catheter, a stent, an embolization coil, or a guidewire. Such an instrument for medical use is produced from a wire form by processing. The present invention includes a wire made of the Au—Cu—Al alloy described above.

A preferred mode of the shape-memory alloy wire is a wire having a diameter of 1 mm or less. The various instruments for medical use described above are passed through human blood vessels, etc., and used for surgery or treatment. In order to make this possible, a wire in the shape of a fine wire is applied. In addition, in consideration of responses to medical instruments microminiaturized more and more in recent years, the diameter of the wire is preferably 500 μm or less, and more preferably 100 μm or less. Incidentally, with respect to the lower limit of the diameter of a wire, the smaller is the better. However, in consideration of its use or workability, the lower limit is preferably 10 μm or more.

The shape-memory alloy wire of the present invention is made of the Au—Cu—Al alloy as described above, and thus preferably has a transformation point and magnetic characteristics (bulk susceptibility) within the above ranges. In addition, the wire also preferably has homogeneity, and it is preferable that there is no variation in the concentration distribution of constituent metals in a wire cross-section. That is, it is preferable that when an arbitrary cross-section (at least either of a longitudinal cross-section and a transverse cross-section) of the wire is analyzed for at least one of Au concentration, Cu concentration, and Al concentration, at least one of the standard deviation of the Au concentration, the standard deviation of the Cu concentration, and the standard deviation of the Al concentration is 1.0 at % or less. Also there, the standard deviation of each element is more preferably 0.8 at % or less, and still more preferably 0.6 at % or less.

In addition, the Vickers hardness of the wire is also required to be 360 Hv or less. Incidentally, this alloy wire preferably has a surface crystal grain size of 5 μm or more and 30 μm or less. This is because moderate workability in processing the wire into an instrument for medical use and moderate elasticity of the formed instrument for medical use should both be exerted. The Vickers hardness of the wire is also preferably 130 Hv or more.

Next, methods for producing the Au—Cu—Al alloy and the alloy wire according to the present invention will be described. The alloy according to the present invention can be basically produced by a melting/casting method. By melting the raw material of each metal to prepare a molten metal and casting the same, a Au—Cu—Al alloy can be obtained. It is relatively easy to obtain a solid solution alloy by a melting/casting method from the Au—Cu—Al alloy in the composition range of the present invention. In addition, by making the cooling rate during casting appropriate, an alloy with excellent homogeneity can be produced.

However, as described above, a Au—Cu—Al alloy has poor toughness in some cases, and may occasionally be an alloy with high hardness and poor workability. Thus, in consideration of the characteristics of a Au—Cu—Al alloy, the present inventors have studied a method for producing an alloy material, which is different from common alloy production methods such as a meting/casting method. Then, as a suitable method for producing the alloy material according to the present invention, they have found a method based on solid-phase diffusion.

The method for producing a Au—Cu—Al alloy is a method for producing a shape-memory alloy, including the steps of: inserting a core material made of metallic Al into a hollow material made of a Au—Cu alloy, closely attaching the two to give a clad material, and heat-treating the clad material at a temperature of 500° C. or more and 700° C. or less, thereby giving a Au—Cu—Al alloy. The method for producing an alloy is a method in which the migration and dissolution of metal elements that constitute an alloy are promoted by solid-phase diffusion, thereby forming a homogeneous Au—Cu—Al alloy.

The fact that an alloy can be formed by solid-phase diffusion itself is known. An example thereof is a so-called bronze process, which is known as a method for producing a superconductive material. As a specific example of the bronze process, a method in which for the production of a refractory superconductive material $Nb_3Sn$, a Nb wire is embedded in a Cu—Sn alloy wire and heat-treated, thereby diffusing Sn over the surface of the Nb wire, is known. This bronze process is also a method for producing an alloy by solid-phase diffusion. Here, when such a conventional method for producing an alloy by solid-phase diffusion is to be applied to the production of the Au—Cu—Al alloy according to the present invention, the following barriers exist.

First, in the present invention, it is required that a Au—Cu—Al alloy, which is a ternary alloy, is produced with excellent homogeneity. When the homogeneity of an alloy is considered, solid-phase diffusion is not necessarily a principle advantageous for alloy production. In the application of solid-phase diffusion, it is necessary to consider the difference in diffusion behavior among a plurality of target metal elements. An extreme difference in diffusion behavior causes heterogeneity in the composition or voids (Kirkendall voids), inhibiting the homogeneity of the alloy.

In addition, in order to ensure the homogeneity of an alloy, it is necessary to suppress the formation of hetero-phase (intermetallic compound) by the constituent metals (Au, Cu, Al) with each other. According to the study by the present inventors, when the metals Au, Cu, and Al are variously combined, in some cases, an intermetallic compound may occasionally be generated. For example, the solid-phase diffusion of metallic Au and metallic Al may result in generating metallic compounds ($Au_2Al$, $Au_4Al$, etc.). Such an intermetallic compound may obstruct the diffusion of elements at the time of alloy formation, impairing the homogeneity.

Further, the above bronze process is usually intended for the formation of a binary alloy ($Nb_3Sn$, etc.). Also in the above example, in the Cu—Sn alloy wire having embedded therein a Nb wire, only Sn is expected to be diffused and alloyed, but Cu does not contribute to alloy formation. The alloy of the present invention is a ternary alloy, and it is preferable not to utilize such a metal that does not contribute to alloy formation.

The present inventors have found the method for producing a shape-memory alloy composed of a Au—Cu—Al alloy in consideration of these problems with solid-phase diffusion.

The method of the present invention is characterized in that a core material made of metallic Al is inserted into and closely attached to a hollow material made of a Au—Cu alloy, and the resulting clad material is used as an object to be treated by solid-phase diffusion. This combination of a Au—Cu alloy and metallic Al dissolves a large number of problem associated with solid-phase diffusion. According to the study by the present inventors, when this combination is applied, and a suitable heat treatment is performed, the diffusion of each metal element suitably proceeds, resulting in the formation of a ternary alloy. In this course, a dense, homogeneous alloy material can be obtained without the formation of voids or the formation of hetero-phase such as an intermetallic compound. Further, the combination of a Au—Cu alloy and metallic Al is also advantageous in terms of workability. This point will be explained below in detail.

Then, the method according to the present invention heat-treats a Au—Cu alloy/metallic Al clad material at an appropriate temperature, thereby making a homogeneous Au—Cu—Al alloy. The heat treatment temperature is specified to be 500° C. or more and 700° C. or less. This is because when the temperature is less than 500° C., solid-phase diffusion advances insufficiently, and an alloy material that is homogeneous in terms of composition cannot be obtained, while when it is more than 700° C., the alloyed wire may be fused. The heat treatment time should be adjusted according to the size of the Au—Cu alloy/metallic Al clad material, and is preferably within a range of 3 minutes or more and 24 hours or less. The time is more preferably 5 minutes or more and 1 hour or less, and still more preferably 5 minutes or more and 30 minutes or less.

Then, in the present invention, the composition of the alloy produced can be adjusted with the composition of a Au—Cu alloy that serves as a hollow material and the composition of metallic Al that serves as a core material. Specifically, with respect to a cross-section of a formed clad material, based on the composition of the Au—Cu alloy and that of metallic Al and the specific gravity of each metal (Au, Cu, Al), the area ratio between the Au—Cu alloy and metallic Al (the thicknesses of the hollow material and the core material) should be adjusted, whereby the alloy composition can be controlled.

Incidentally, the metallic Al to serve as a core material in this production method means pure Al, which has a purity of 99.9 at % or more and 100 at % or less. The purity of metallic Al is more preferably 99.99 at % or more. In addition, the hollow material made of a Au—Cu alloy is a tubular structure having a cavity inside. The transverse cross-sectional shape of the hollow material is not particularly limited, and may be any of circular, elliptical, and rectangular. The composition of the Au—Cu alloy is determined together with the dimension (thickness) of the hollow material in consideration of the composition of the ternary alloy to be produced and the composition of metallic Al. When the Au—Cu—Al alloy according to the present invention (Cu: 20 at % or more and 40 at % or less, Al: 15 at % or more and 30 at % or less, balance: Au) is considered, only as a guide, the Au concentration of the Au—Cu alloy is 50 at % or more and 68 at % or less. In addition, when they are formed into a clad material, the area ratio is preferably such that the area ratio of the metallic Al area/the Au—Cu alloy area is 0.3 or more and 0.4 or less. In addition, when the metallic Al to serve as a core material is inserted into the hollow material made of a Au—Cu alloy, the both materials do not have to be closely attached at that time. That is, the cross-sectional area of the hollow part of the hollow material does not have to agree with the cross-sectional area of the core material. This is because the hollow material may be processed and closely attached after insertion.

Then, the method for producing a Au—Cu—Al alloy according to the present invention is also suitable as a method for producing a shape-memory alloy wire. The method for producing a shape-memory alloy wire is a method including the steps of:

inserting a wire made of metallic Al into a tube made of a Au—Cu alloy to give a clad tube, drawing the clad tube at least once to give a clad wire, and then heat-treating the clad wire at a temperature of 500° C. or more and 700° C. or less, thereby giving a Au—Cu—Al alloy wire.

In contrast to the method for producing an alloy material described above, in the method for producing a wire, a wire made of metallic Al is inserted into a tube made of a Au—Cu alloy to form a clad tube. The meanings of the tube and the wire are basically the same as for the hollow material and the clad material. In the present invention, a wire having a small diameter is produced. Therefore, a tube having a relatively small outer diameter, that is, about 2 mm or more and 5 mm or less, is used. Incidentally, when the metallic Al wire is inserted into the Au—Cu alloy tube, the two do not need to be closely attached.

Then, in the method for producing a wire, the clad tube having a Au—Cu alloy/metallic Al structure is drawn into a clad wire. That is, a wire is formed before alloying. This step is a characteristic part, in which with respect to a tube having a Au—Cu alloy/metallic Al clad structure, the advantages based on the combination of the materials described above and also the advantages of each material are utilized, thereby efficiently producing an alloy wire with improved fineness.

That is, the Au—Cu alloy and metallic Al are each a metal/alloy with excellent workability. Their workability is higher than when they have become a ternary alloy through solid-phase diffusion. Therefore, when drawing is performed before alloying, a wire with a desired wire diameter can be produced without the risk of breakage.

In addition, the combination of a Au—Cu alloy/metallic Al is also useful in that the wire having a desired alloy composition can be produced. As described above, in the method for producing an alloy of the present invention that utilizes solid-phase diffusion, by adjusting the ratio between the cross-sectional area of a Au—Cu alloy and the cross-sectional area of metallic Al in a cross-section of a clad tube (clad material), the composition in a formed ternary alloy can be controlled. However, when the area ratio in the clad tube significantly changes upon drawing, an excessive error occurs in the alloy composition of a formed wire. According to the study by the present inventors, in a clad tube made of a combination of a Au—Cu alloy/metallic Al, changes in the area ratio of each layer are extremely small even after repeated drawing. Further, even when such a clad tube is formed into a wire and then heat-treated, an alloy wire having a target composition can be achieved. This is presumably because of the excellent workability that the Au—Cu alloy and metallic Al each have, and this combination has a useful effect in terms of adjusting the composition of an alloy wire.

As described above, the method for producing a shape-memory alloy wire according to the present invention is preferable as a method for producing a wire that constitutes an instrument for medical use, which is supplied in the form of a wire.

The fundamental principle and steps of the method for producing a wire are the same as in the above method for producing an alloy material, and the composition should be adjusted with the area ratio between the Au—Cu alloy layer and the metallic Al layer in a cross-section of a formed clad tube. The guides for the composition of the Au—Cu alloy tube, that of the metallic Al wire, and the like are the same as above.

With respect to drawing after forming a clad tube, the specific mode of the processing method is not particularly limited. The processing may be any of swaging, rolling (grooved-roll rolling), die drawing, and extrusion, and may also be a combination thereof. Then, drawing is performed at least once, and the number of times and the processing method should be adjusted according to the desired wire diameter. In this drawing, the processing ratio in each time of drawing (per pass) is specified to be 3% or more and 15% or less in terms of the reduction in cross-sectional area. This is for ensuring the production efficiency and avoiding the breakage. In addition, the processing temperature of drawing is preferably 10° C. or more and 100° C. or less. This is for suppressing structural changes during processing. However, in the drawing intended for solid-phase diffusion (alloying) described below, this processing temperature condition is not applied.

After the clad wire is drawn into a wire having a desired wire diameter to be produced, a heat treatment is conducted to cause solid-phase diffusion to provide a ternary alloy wire. As above, the heat treatment temperature specified to be 500° C. or more and 700° C. or less. The heat treatment time is preferably within a range of 3 minutes or more and 24 hours or less.

In addition, by adjusting the processing temperature of drawing, the heat treatment for the solid-phase diffusion of the clad wire is allowed to proceed at the same time with the processing. This method for producing a shape-memory alloy wire is a method including the steps of: inserting a wire made of metallic Al into a tube made of a Au—Cu alloy to give a clad tube; and drawing the clad tube at least once, in which at least once of the drawing is warm working at 500° C. or more and 700° C. or less, thereby producing a Au—Cu—Al alloy wire.

Thus, when the drawing and the alloying heat treatment are performed at the same time, the heat treatment step separately performed after the processing can be omitted. Also in this method, drawing is performed more than once, and it is specified that at least once of the drawing is warm working. Preferably, warm working is performed in the final drawing step. The processing temperature in the warm working is also specified to be 500° C. or more and 700° C. or less. However, for reasons of the processing device, in the case of applying warm working, the processing temperature is preferably 550° C. or more. Incidentally, except for that the drawing is partially warm working, other conditions (heating time, etc.) can be the same as for the method for producing a shape-memory alloy wire described above, in which a wire is heat-treated after the processing.

Through the above methods for producing a shape-memory alloy wire, a wire made of a homogeneous Au—Cu—Al alloy is produced. By suitably cutting this wire and processing the same, various instruments for medical use can be produced.

The present invention can be hoped to be applied as a material for medical use to various instruments for medical use. Specifically, applications to instruments for medical use, such as embolization coils, dental braces, clasps, dental implants, clips, staples, catheters, stents, bone plates, and guidewires, are possible.

Advantageous Effects of the Invention

As described above, the shape-memory alloy according to the present invention is an alloy that is Ni-free and has biocompatibility, and also is capable of developing the shape-memory effect at a temperature equal to or lower than a human body temperature. In addition, the alloy also has the possibility of developing superelasticity in the ambient temperature range. Then, the present invention is also characterized in that its bulk susceptibility is controlled to be within an appropriate range, and thus the alloy is artifactless in a magnetic environment. Therefore, the alloy is preferable as a constituent material for various instruments for medical use.

Incidentally, Au has biocompatibility, and its X-ray contrast is also excellent. In treatment with a stent or the like, the position of the instrument or the like is confirmed by use of X-ray together. Also from this point of view, the Au—Cu—Al alloy of the present invention is suitable as a material for medical use.

DESCRIPTION OF EMBODIMENTS

Hereinafter, embodiments of the present invention will be described.

First Embodiment

In this embodiment, a wire made of a shape-memory alloy composed of a Au-25 at % Cu-25 at % Al alloy was produced. In addition, in the production of the shape-memory alloy wire, while adjusting the heat treatment conditions and the like, the possibility of alloy wire production was examined.

First, into a Au—Cu alloy tube (outer diameter: 3.53 mm, inner diameter: 2.5 mm) made of a Au-33.33 at % Cu alloy (a Au-13.89 mass % Cu alloy), an Al wire (purity: 99.99%) having a wire diameter of 1.5 mm was inserted and swaged, thereby a clad tube having an outer diameter of 2.6 mm was prepared. This clad tube has, in its transverse cross-section, from the ratio between the cross-sectional area of the Au—Cu alloy tube and the cross-sectional area of the Al wire, an apparent composition of a Au-25 at % Cu-25 at % Al alloy (Au-13.12 mass % Cu-5.57 mass % Al alloy).

The clad tube (a Au-33.33 at % Cu alloy/Al tube, wire diameter: 2.6 mm) prepared above was drawn into a wire (clad wire) having a wire diameter of 100 μm. Drawing was repeatedly performed such that the reduction in cross-sectional area per pass was 10%. The processing temperature was room temperature (25° C.).

The clad wire having a wire diameter of 100 μm (Au-33.33 at % Cu alloy/Al) was heat-treated to provide a Au—Cu—Al alloy wire. At this time, as the heat treatment temperature conditions, temperatures were set at intervals 50° C. from 550° C. to 750° C., and the relationship between a temperature and the possibility of alloy formation was evaluated. In addition, the heat treatment time was set at 5 minutes for each heat treatment temperature.

In the course of alloy wire production described above, during the drawing from a clad wire (wire diameter: 100 μm) to a clad tube (wire diameter: 2.6 mm), the cross-section after each processing pass was observed, and the areas of the Au—Cu alloy layer and the Al wire were measured. In this measurement, a photograph of the alloy cross-section was analyzed under a digital microscope (LEICA DMS1000), and the area of each layer was measured by use of a built-in area calculation tool. Then, the occupancy of the Al wire portion in the cross-section was calculated.

subjected to several passes of drawing, changes in the area ratio of each layer are extremely small. This shows that adjusting the area (area ratio) of each layer at the time of the formation of a clad tube (clad material) allows the composition of the finally produced alloy wire to be controlled. This is one of advantages of employing a combination of a Au—Cu alloy tube and an Al wire.

Figure 3:
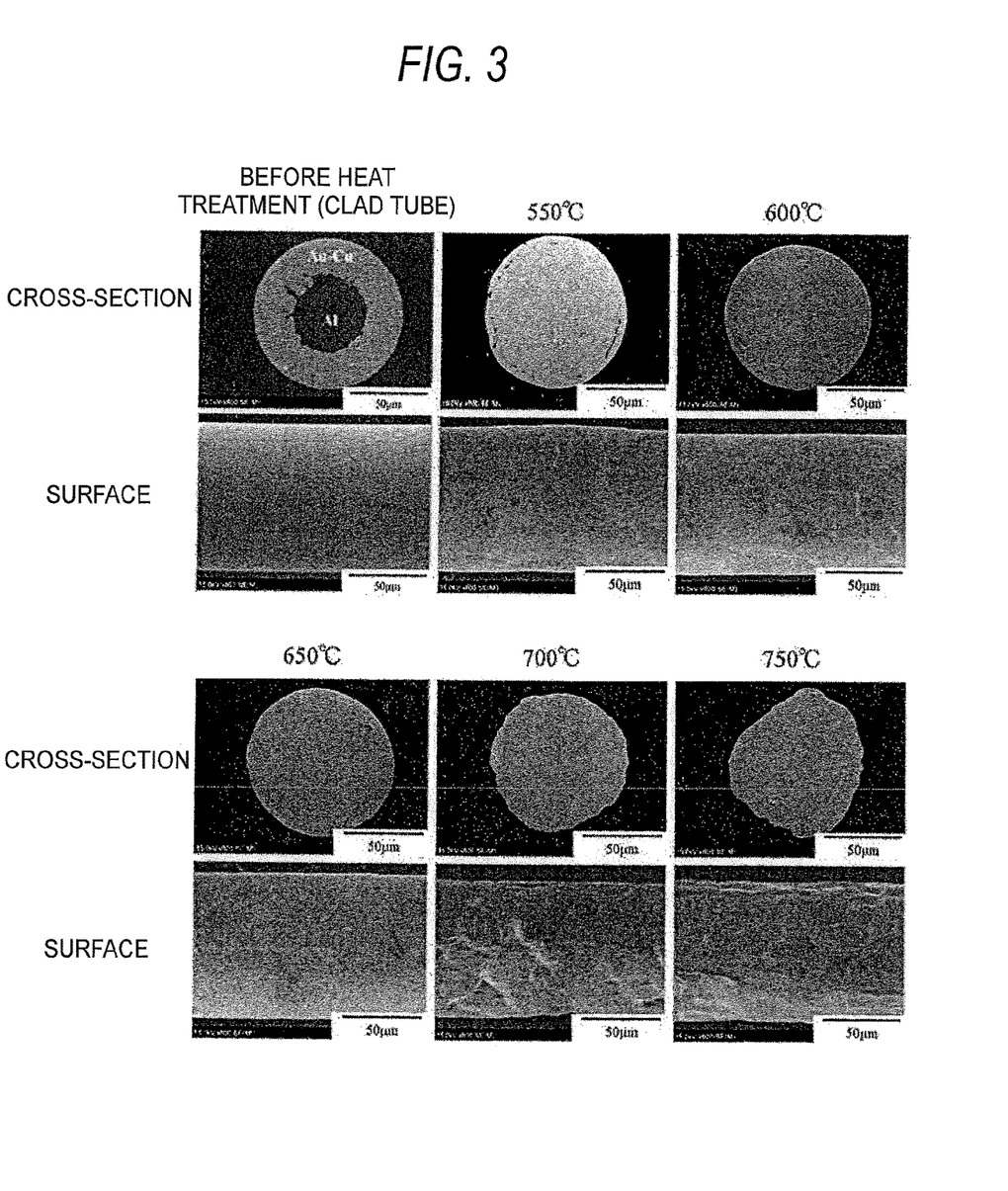
FIG. 3 illustrates SEM images of a cross-section and the outer surface of a wire heat-treated from a clad wire at each heat treatment temperature.

Then, FIG. 3 shows, with respect to clad wires drawn to a wire diameter of 100 μm, a SEM image of a cross-section (transverse cross-section) of each wire after a heat treatment at a heat treatment temperature from 550° C. to 750° C., together with a SEM image of the outer surface of the wire. From FIG. 3, it can be observed that in cross-sections of the wires heat-treated at 550° C. or more, the images have uniform contrast, indicating the completion of alloying by solid-phase diffusion.

Thus, a cross-section (transverse cross-section) of each wire heat-treated at 550° C. or more was subjected to element mapping by EDS. As a result, it was confirmed that in the entire cross-section of the wire, the elements of Au, Cu, and Al were each present. As a result, it was confirmed that as a result of the heat treatment at 550° C. or more, a monolayer ternary alloy (Au—Cu—Al alloy) was formed from the two-phase clad wire. Then, such a wire cross-section was optionally subjected to quantitative analysis by EDS. As a result, it was confirmed that in any point, the alloy was a Au-25±1 at % Cu-25±1 at % Al alloy.

Further, with respect to a cross-section (transverse cross-section) of each wire heat-treated at 550° C. or more, in order to evaluate the variation in the composition, a plurality of points from the central part of the wire to its edge were subjected to quantitative analysis (at %) for Au concentration. In the quantitative analysis, an arbitrary transverse cross-section of the wire was analyzed by EDX at a central point and also four points at intervals of 16 μm from the central point to each edge. The results are shown in Table 1.

TABLE 1

| Heat Treatment Temperature | Au Concentration (at %) | | | | | | | | | Average (at %) | Standard Deviation (at %) |
|---|---|---|---|---|---|---|---|---|---|---|---|
| | Edge | | | | Center | | | | Edge | | |
| | 1 | 2 | 3 | 4 | 5 | 6 | 7 | 8 | 9 | | |
| 550° C. | 50.45 | 50.25 | 50.33 | 51.34 | 51.98 | 50.22 | 51.07 | 50.69 | 50.81 | 50.79 | 0.55 |
| 600° C. | 50.64 | 51.99 | 51.31 | 50.49 | 50.56 | 51.71 | 50.53 | 51.58 | 51.08 | 51.10 | 0.54 |
| 650° C. | 51.22 | 50.29 | 51.47 | 51.12 | 50.89 | 51.77 | 50.62 | 50.84 | 51.33 | 51.06 | 0.43 |
| 700° C. | 51.29 | 51.14 | 50.99 | 51.36 | 51.39 | 50.78 | 50.87 | 51.29 | 51.31 | 51.16 | 0.21 |
| 750° C. | 51.35 | 51.32 | 51.36 | 50.99 | 51.16 | 50.79 | 50.79 | 51.56 | 51.28 | 51.18 | 0.25 |

Figure 1:
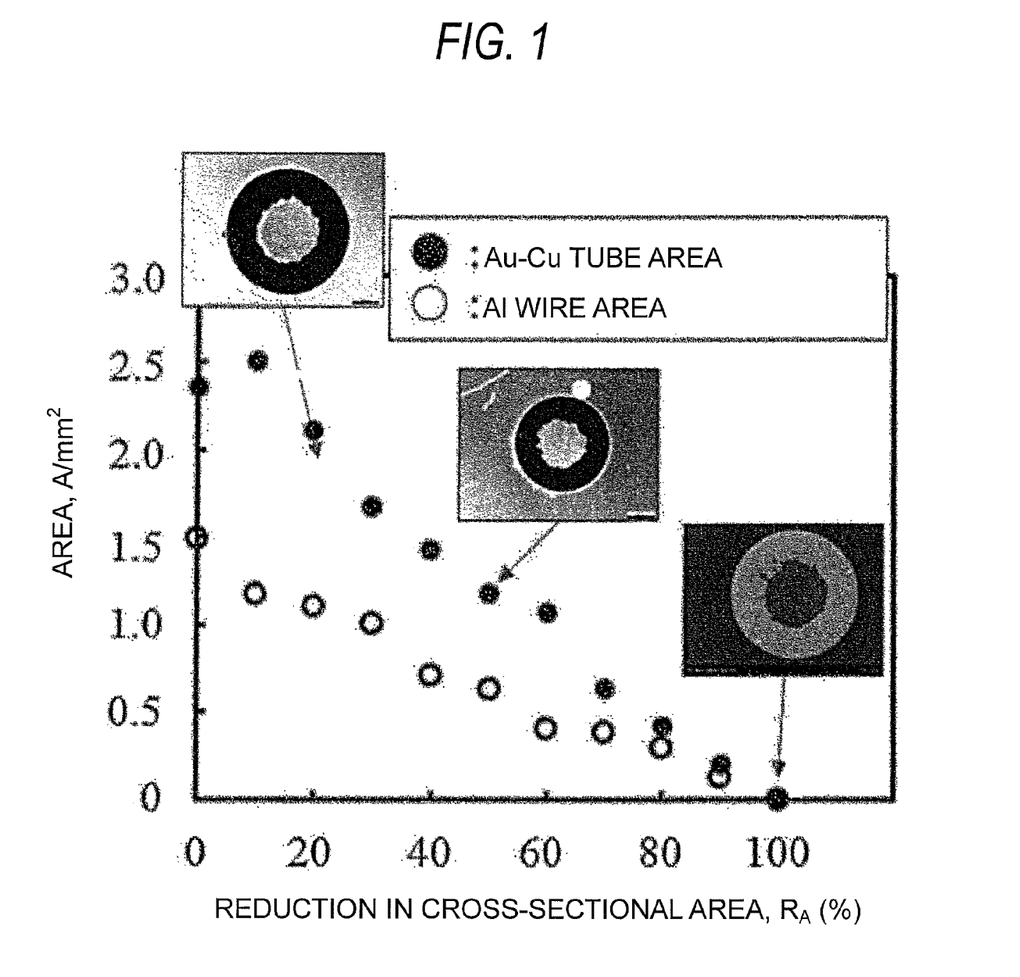
FIG. 1 is a diagram showing changes in the Au—Cu alloy layer area and the Al wire area in a wire cross-section per processing pass in the drawing step of the first embodiment.
Figure 2:
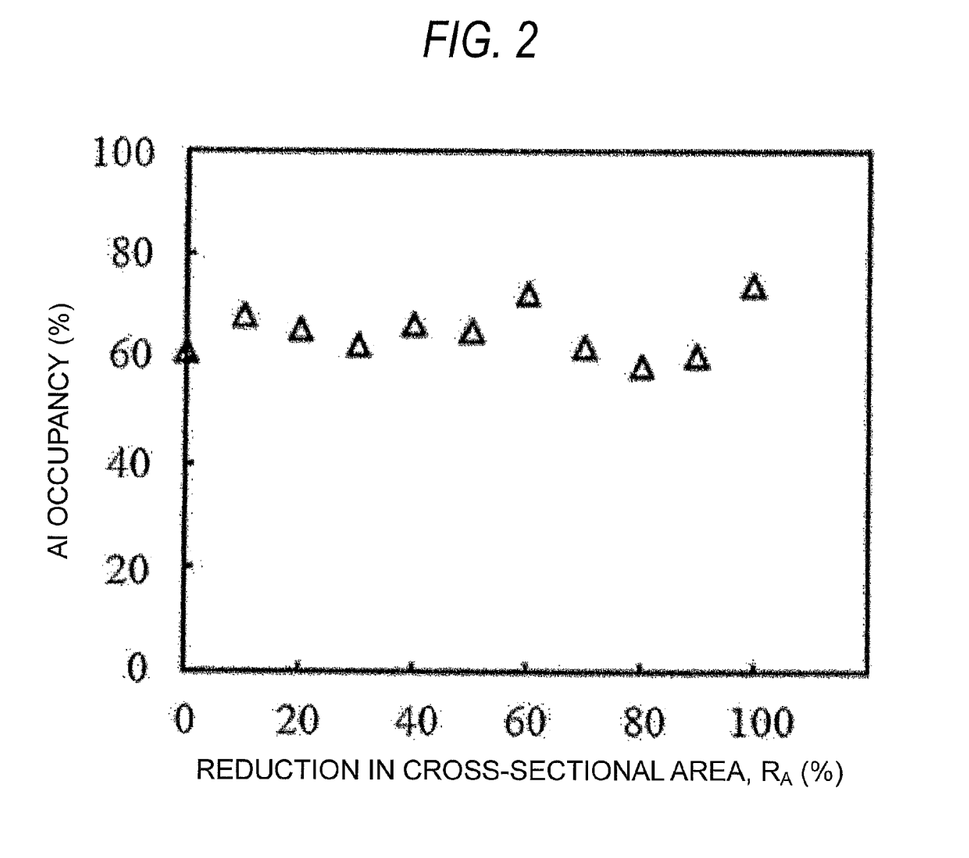
FIG. 2 is a diagram showing the occupancy of the Al wire in a wire cross-section per processing pass in the drawing step of the first embodiment.

FIG. 1 is a diagram showing changes in the Au—Cu alloy layer area and the Al wire area in the cross-section (transverse cross-section) of the workpiece for every processing pass of the drawing step. In addition, FIG. 2 is a diagram showing changes in the occupancy of the Al wire portion in the cross-section of the workpiece for every processing pass of the drawing step. It can be understood from FIG. 1 that, with the progress of drawing (an increase in the reduction in cross-sectional area), the areas of the Au—Cu alloy layer and the Al wire decrease, but their decreases are relatively linear relative to the increase in the reduction in cross-sectional area. This can also be understood from FIG. 2, where there is no significant change in the area occupancy of the Al wire even though the reduction in cross-sectional area increases. That is, even when a clad tube formed of a combination of a Au—Cu alloy tube and an Al wire is It was confirmed from Table 1 that the variation in the Au concentration is small in all the alloy wires, (standard deviation: 0.6 at % or less), and that they were Au—Cu—Al alloys with excellent homogeneity.

Next, with respect to the alloy wires heat-treated at 550° C. or more, each test piece was subjected to hardness measurement and the measurement/evaluation of the crystal grain size (average) of the wire outer surface, shape-memory characteristics (transformation temperature), and bulk susceptibility. The evaluation methods for the characteristics were as follows.

Hardness Measurement

The central part of a cross-section (transverse cross-section) of each wire was subjected to hardness measurement by use of a Vickers hardness tester (Hardness Testing Machine HM-200: manufactured by Mitutoyo Corporation). The measurement was performed at room temperature under a load of 10 gf.

Crystal Grain Size Measurement

Based on the SEM images of FIG. 3, with respect to the outer surface of each alloy wire, a crystal grain was arbitrarily selected, and two line segments orthogonal thereto were drawn. The width of the grain boundary was measured from each line segment, and their average was defined as the crystal grain size. This operation was performed on three arbitrary crystal grains, and the average of the particle sizes of the three crystal grains was defined as the crystal grain size of each wire surface.

Shape-Memory Characteristics

By the DSC (differential scanning calorimetry) method, the transformation temperature (Ms) of each alloy wire was measured. The measurement conditions were such that the temperature rise/fall rate from −150° C. to 150° C. was 10° C./min. With respect to the measured transformation temperatures, alloys having a transformation temperature of 315 K (42° C.) or less were rated as "excellent (⊙)", that is, as having a possibility of the preferred shape-memory effect development to be achieved by the present invention. Meanwhile, those having a transformation temperature of more than 315 K (42° C.) was rated as "inappropriate (×)".

Bulk Susceptibility (Artifactless)

By use of a magnetic balance, the bulk susceptibility (Xvol) of each alloy wire was measured. The measurement was performed at room temperature. With respect to the measured bulk susceptibility, the deviation from the susceptibility of water (−9 ppm) was calculated, and ±5 ppm or less was rated as "excellent (⊙)", ±15 ppm or less was rated as "good (○)", and more than ±15 ppm was rated as "inappropriate (×)".

The measurement results and evaluation results of the characteristics are shown in Table 2.

TABLE 2

| Heat Treatment Temperature | Hardness (Hv) | Average Particle Size (μm: surface) | Shape-memory characteristics | Bulk Susceptibility |
|---|---|---|---|---|
| 550° C. | 161 | 7 | ⊙ | ○ |
| 600° C. | 155 | 12 | ⊙ | ○ |
| 650° C. | 163 | 12 | ⊙ | ○ |
| 700° C. | 140 | 24 | ⊙ | ○ |
| 750° C. | 140 | 24 | ⊙ | ○ |

From Table 2, it was confirmed that the shape-memory alloy wire made of a Au-25 at % Cu-25 at % Al alloy produced in this embodiment was excellent in terms of both shape-memory characteristics (transformation temperature) and artifactlessness (bulk susceptibility). These alloy wires each had a hardness of 360 Hv or less. In addition, in each case, crystal grains of the wire surface had an average particle size of 30 μm or less. However, with respect to the wire heat-treated at 750° C., from its cross-section image, the deterioration of the wire surface shape was observed. This is presumably because of the progress of the diffusion phenomenon more than necessary. In addition, a heat treatment at 750° C. has a possibility of fusing the wire.

Second Embodiment

In this embodiment, shape-memory alloy wires made of Au—Cu—Al alloys with various compositions were produced, and their characteristics were evaluated.

The method for producing an alloy wire in this embodiment is the same as in the first embodiment. Here, an Al wire (purity: 99.99%) having a wire diameter of 1.5 mm was inserted into a Au—Cu alloy tube with an adjusted Cu concentration (outer diameter: 3.53 mm, inner diameter: 2.5 mm), and swaged to give a clad tube, followed by drawing. Also here, the composition of the alloy wire was preliminarily set, and the ratio between the cross-sectional area of the Au—Cu alloy tube and the cross-sectional area of the Al wire in the clad tube was adjusted such that the apparent composition agreed.

Drawing was repeatedly performed such that the reduction in cross-sectional area per pass was 10% and the wire diameter reached 100 μm. The drawing temperature was room temperature. Then, the clad wire having a wire diameter of 100 μm (Au—Cu alloy/Al) was heat-treated at 600° C. for 5 minutes to give a Au—Cu—Al alloy wire.

With respect to the produced Au—Cu—Al alloy wire, while confirming that the wire was single-phase by the SEM observation of a cross-section, it was confirmed by EDS that the composition was homogeneous like the alloy wire of the first embodiment. Then, by the same method as in the first embodiment, the analysis of Au concentration (average and standard deviation analysis) in an arbitrary cross-section (transverse cross-section), the measurement of hardness, the measurement of the crystal grain size of the outer surface, and the measurement and evaluation of shape-memory characteristics and bulk susceptibility were performed. The results are shown in Table 3.

TABLE 3

| | | | | Measurement results | | | | | | |
|---|---|---|---|---|---|---|---|---|---|---|
| | Composition (at %) | | | Au concentration (at %) | | Average particle size (μm) | Vickers hardness (Hv) | Shape-memory characteristics Ms | | Bulk susceptibility (artifact) Xvol |
| No. | Au | Cu | Al | Average | Standard deviation | | | (K) | Evaluation | (ppm) | Evaluation |
| 1 | Balance | 27.0 | 18.0 | 55.1 | 0.5 | 14 | 209 | 265 | ⊙ | −3.6 | ○ |
| 2 | | 28.0 | 22.0 | 49.8 | 0.6 | 11 | 137 | 289 | ⊙ | −0.8 | ○ |
| 3 | | 25.0 | 25.0 | 51.1 | 0.5 | 12 | 155 | 292 | ⊙ | −2.8 | ○ |
| 4 | | 30.0 | 25.0 | 45.1 | 0.4 | 15 | 224 | 290 | ⊙ | −1.5 | ○ |
| 5 | | 35.0 | 25.0 | 40.2 | 0.4 | 13 | 343 | 296 | ⊙ | −1.9 | ○ |

TABLE 3-continued

| | Composition (at %) | | | Au concentration (at %) | | Average particle size (μm) | Vickers hardness (Hv) | Shape-memory characteristics | | Bulk susceptibility (artifact) | |
|---|---|---|---|---|---|---|---|---|---|---|---|
| | | | | | Standard | | | Ms | | Xvol | |
| No. | Au | Cu | Al | Average | deviation | | | (K) | Evaluation | (ppm) | Evaluation |
| 6 | | 31.3 | 28.0 | 40.7 | 0.6 | 17 | 358 | 276 | ☉ | −7.9 | ☉ |
| 7 | | 45.0 | 25.0 | 29.8 | 0.5 | 19 | 128 | — | — | 7.0 | X |

*The heat treatment temperature for each clad wire is 600° C.
*No. 3 is an alloy of the first embodiment.

It was confirmed from Table 3, preferred transformation temperatures (Ms) and bulk susceptibilities (Xvol) were measured in the Au—Cu—Al alloys composed of 20 at % or more and 40 at % or less Cu and 15 at % or more and 30 at % or less Al (No. 1 to No. 6), and thus simultaneous realization of the development of preferred shape-memory characteristics and artifactlessness would be possible. In some of these Au—Cu—Al alloy wires, the transformation temperature was equal to or lower than ambient temperature, and the development of superelasticity was seemed to be possible. Meanwhile, the development of shape-memory characteristics was not observed in the Au—Cu—Al alloy having a high Cu content (No. 7).

The alloy having the highest content of Al in this embodiment (No. 6) has relatively high hardness, but is particularly excellent in terms of shape-memory characteristics and bulk susceptibility. The hardness of an alloy material may affect the workability. Therefore, in terms of workability alone, it can be said that the alloy of this composition has a problem with practical use. However, according to the method for producing an alloy wire of the present invention, prior to the formation of a Au—Cu—Al alloy, which tends to increase hardness, a clad wire made of a Au—Cu alloy and Al is processed into a wire having a desired diameter. That is, it can be seen that the method of the present invention is useful in that even an alloy with a composition concerned with workability can be made into a wire having a desired wire diameter. Incidentally, it was confirmed that the shape-memory alloy wires in this example (No. 1 to No. 6) each had a small variation in the Au concentration in a transverse cross-section (standard deviation: 0.6 at % or less), and that they were homogeneous alloys. In each case, crystal grains of the wire surface had an average particle size of 30 μm or less.

INDUSTRIAL APPLICABILITY

The shape-memory alloy according to the present invention is an alloy that develops a shape-memory effect in an appropriate temperature range and also has appropriate bulk susceptibility, and can also be artifactless in a magnetic environment. Further, the alloy does not contain Ni and thus has biocompatibility, which is an indispensable requirement as a material for medical use, also has excellent X-ray contrast. The present invention can be hoped to be applied to various medical instruments.

The invention claimed is:

1. A shape-memory alloy wire consisting of a Au—Cu—Al alloy having 20 at % or more and 40 at % or less Cu and 15 at % or more and 30 at % or less Al, with the balance being Au and inevitable impurities, wherein the wire has a diameter of 1 mm or less, a Au concentration analyzed with respect to an arbitrary cross-section has a standard deviation of 1.0 at % or less, and the shape-memory alloy has a bulk susceptibility of −24 ppm or more and 6 ppm or less, and has a Vickers hardness of 360 Hv or less.

2. The shape-memory alloy wire according to claim 1, wherein the wire has a diameter of 10 um or more and 100 um or less.

3. An embolization coil, a dental brace, a clasp, a dental implant, a clip, a staple, a catheter, a stent, a bone plate, or a guidewire comprising the shape-memory alloy defined in claim 1.

4. A method for producing the shape-memory alloy defined in claim 1, comprising the steps of:

inserting a core material made of metallic Al into a hollow material made of a Au—Cu alloy, and closely attaching the both materials provide a clad material; and heat-treating the clad material at a temperature of 500° C. or more and 700° C. or less, thereby providing a Au—Cu—Al alloy.

5. A method for producing the shape-memory alloy wire defined in claim 1, comprising the steps of:

inserting a wire made of metallic Al into a tube made of a Au—Cu alloy to provide a clad tube; and drawing the clad tube at least once to give a clad wire, and then heat-treating the clad wire at a temperature of 500° C. or more and 700° C. or less, thereby preparing a Au—Cu—Al alloy wire.

6. A method for producing the shape-memory alloy wire defined in claim 1, comprising the steps of:

inserting a wire made of metallic Al into a tube made of a Au—Cu alloy to give a clad tube; and drawing the clad tube at least once, wherein at least once of the drawing is warm working at 500° C. or more and 700° C. or less, thereby producing a Au—Cu—Al alloy wire.

7. A method for producing the shape-memory alloy wire defined in claim 2, comprising the steps of:

inserting a wire made of metallic Al into a tube made of a Au—Cu alloy to provide a clad tube; and drawing the clad tube at least once to give a clad wire, and then heat-treating the clad wire at a temperature of 500° C. or more and 700° C. or less, thereby preparing a Au—Cu—Al alloy wire.

8. A method for producing the shape-memory alloy wire defined in claim 2, comprising the steps of:

inserting a wire made of metallic Al into a tube made of a Au—Cu alloy to give a clad tube; and drawing the clad tube at least once, wherein
at least once of the drawing is warm working at 500° C. or more and 700° C. or less, thereby producing a Au—Cu—Al alloy wire.

* * * * *